(12) United States Patent
Chang et al.

(10) Patent No.: US 12,306,189 B2
(45) Date of Patent: May 20, 2025

(54) DETECTION METHOD AND SYSTEM FOR DETECTING BIOLOGICAL SAMPLES

(71) Applicant: ACADEMIA SINICA, Taipei (TW)

(72) Inventors: Huan-Cheng Chang, Taipei (TW); Yuen-Yung Hui, Taipei (TW); Hsin-Hung Lin, New Taipei (TW); Oliver Y. Chen, Taipei (TW)

(73) Assignee: ACADEMIA SINICA, Taipei (TW)

( * ) Notice: Subject to any disclaimer, the term of this patent is extended or adjusted under 35 U.S.C. 154(b) by 505 days.

(21) Appl. No.: 17/502,399

(22) Filed: Oct. 15, 2021

(65) Prior Publication Data

US 2022/0120757 A1 Apr. 21, 2022

Related U.S. Application Data

(60) Provisional application No. 63/093,854, filed on Oct. 20, 2020.

(51) Int. Cl.
*G01N 33/58* (2006.01)
*G01N 21/64* (2006.01)
*G01N 33/543* (2006.01)

(52) U.S. Cl.
CPC ....... *G01N 33/582* (2013.01); *G01N 21/6428* (2013.01); *G01N 33/543* (2013.01); *G01N 2021/6439* (2013.01)

(58) Field of Classification Search
CPC ............. G01N 33/582; G01N 21/6428; G01N 33/543; G01N 2021/6439
See application file for complete search history.

(56) References Cited

U.S. PATENT DOCUMENTS 8,551,408 B2 10/2013 Beaudet et al.

FOREIGN PATENT DOCUMENTS

| CN | 101375150 A | 2/2009 |
| CN | 108064244 A | 5/2018 |

OTHER PUBLICATIONS

Moyano, Amanda et al. "Magnetic Lateral Flow Immunoassays." Diagnostics (Basel, Switzerland) vol. 10,5 288. May 8, 2020, doi:10.3390/diagnostics10050288 (Year: 2020).*
Miller, Benjamin S et al. "Spin-enhanced nanodiamond biosensing for ultrasensitive diagnostics." Nature vol. 587,7835 (2020): 588-593. doi:10.1038/s41586-020-2917-1 (Year: 2019).*
Li, Dongfang. "Development of immunoassay screening methods using long wavelength fluorescence." (2004). Loughborough University Doctoral Thesis. https://hdl.handle.net/2134/12905. (Year: 2004).*
Van Reenen, Alexander et al. "Integrated lab-on-chip biosensing systems based on magnetic particle actuation—a comprehensive review." Lab on a chip vol. 14,12 (2014): 1966-86. doi:10.1039/c3lc51454d (Year: 2014).*
Kim, N Y et al. "A reusable robust radio frequency biosensor using microwave resonator by integrated passive device technology for quantitative detection of glucose level." Biosensors & bioelectronics vol. 67 (2015): 687-93. doi:10.1016/j.bios.2014.10.021 (Year: 2014).*

* cited by examiner

*Primary Examiner* — Elizabeth C. Kemmerer
*Assistant Examiner* — McKenzie A Dunn
(74) *Attorney, Agent, or Firm* — MUNCY, GEISSLER, OLDS & LOWE, P.C.

(57) ABSTRACT

The present disclosure discloses a detection method and a detection system for detecting an object of interest in a biological sample. The detection method comprises the following steps: providing a detection kit comprising a detection carrier and a reporter, wherein the detection carrier comprises a coating protein having a recognition site for binding the object of interest, the reporter including a spin luminescent material; mixing the reporter and the biological sample and loading the mixture onto the detection carrier; placing the detection carrier with the mixture of the reporter molecule and the biological sample in a time-varied physical field; irradiating a detection carrier placed in the time-varied physical field with an excitation light to excite the spin luminescent material to generate a fluorescence signal modulated by the time-varied physical field; and receiving and analyzing the fluorescence signal.

4 Claims, 8 Drawing Sheets

DETECTION METHOD AND SYSTEM FOR DETECTING BIOLOGICAL SAMPLES

BACKGROUND

1. Technical Field

The present disclosure is related a detection method and a detection system, specifically to a detection method and a detection system for detecting of objects of interest in biological samples.

2. Description of the Related Art

Regarding the detection methods for detecting a specific target in a biological sample, such as the detection of antigens (e.g., deoxyribonucleic acid (DNA), proteins or microbes, etc.) or antibodies, an immunoassay is often used. According to user requirements and situations, many different detection products are applied to the immunoassay on the market.

If the detection result must be known in a short time, an immunochromatographic test (ICT) strip is often used for rapid detection. In the immunochromatographic test, an antibody, which can be conjugated with a target (i.e., an antigen), is first deposited on (bound to) a test strip, and the deposited site is called a test line. Then a biological sample and an antibody with a colored marker are mixed. The common colored markers include colored latex particles, colloid gold particles, or other dyes. When the target is present in the biological sample, the antibody with the colored marker binds the target. When the mixture flows through the test line of the test strip, the antibody on the test strip can also bind the target, and the test line becomes colored due to the colored marker. However, this kind of coloration has to be observed with the naked eye, has poor sensitivity, and cannot be applied to the detection of trace targets (i.e., antigens).

A common immunoassay for detecting trace targets uses an enzyme to amplify the signal, as in the case of the enzyme-linked immunosorbent assay (ELISA). In addition to the antibody that can bind to the antigen, ELISA also requires the use of an enzyme-linked secondary antibody and a colorimetric substrate (i.e., a coloring agent). The amount of the target in the biological sample can be quantified by measuring the absorbance of the colorimetric substrate at a specific wavelength. However, the procedure of ELISA is cumbersome; for example, the enzyme-linked secondary antibodies need to be obtained and unbound antibodies need to be washed away. Insufficient washing steps or a high concentration of secondary antibodies may cause high background interference.

SUMMARY

In view of the problems mentioned above, the main purpose of the present disclosure is to provide a detection method and a detection system for detecting a biological sample through application of a spin luminescent material in an immunoassay as a reporter and the modulation of the characteristics of the spin luminescent materials by a time-varied physical field such that the problem of poor sensitivity or the cumbersome procedures of conventional immunoassays can be solved.

To achieve the above objective, the present disclosure provides a detection method for detecting an object of interest in a biological sample. The detection method comprises the following steps: providing a detection kit, which comprises a detection carrier and a reporter, wherein the detection carrier comprises a coating protein having a recognition site for binding the object of interest and the reporter comprises a spin luminescent material; mixing the reporter and the biological sample, and loading the mixture onto the detection carrier; placing the detection carrier with the mixture of the reporter molecule and the biological sample in a time-varied physical field; irradiating the detection carrier placed in the time-varied physical field with an excitation light to excite the spin luminescent material to generate a fluorescence signal modulated by the time-varied physical field; and receiving and analyzing the fluorescence signal.

According to an embodiment of the present disclosure, the object of interest in the biological sample is labeled by the reporter, and the reporter binds to the coating protein via the object of interest.

According to an embodiment of the present disclosure, before the step of placing the detection carrier in a time-varied physical field, the detection method further comprises the step of removing the reporter which is unbound to the coating protein.

According to an embodiment of the present disclosure, the reporter further comprises a capture antibody which has a recognition site that binds to the object of interest. The capture antibody binds to the spin luminescent material, and the reporter labels the object of interest in the biological sample by the capture antibody.

According to an embodiment of the present disclosure, the spin luminescent material comprises a fluorescent nanodiamond, an organic dye-labeled magnetic bead, or a rare-earth metal ion doped magnetic bead.

According to an embodiment of the present disclosure, the spin luminescent material comprises a plurality of spin luminescent particles, and a diameter of each of the spin luminescent particles is between 1 nm and 1 mm.

According to an embodiment of the present disclosure, the detection carrier comprises a solid phase substrate.

According to an embodiment of the present disclosure, the time-varied physical field comprises an alternating current magnetic field or a microwave field.

According to an embodiment of the present disclosure, a frequency of the alternating current magnetic field is between 1 Hz and 1 MHz, a root mean square value of an amplitude of the alternating current magnetic field is between 1 G and 10000 G, and a frequency of the microwave field is between 0.1 MHz and 10 GHz.

According to an embodiment of the present disclosure, the step of analyzing the fluorescence signal further comprises comparing the fluorescence signal with a quantitative standard curve to quantify a concentration of the object of interest.

To achieve the above objective, the present disclosure further provides a detection system, which is used with a detection kit for detecting an object of interest in a biological sample. The detection kit comprises a detection carrier and a reporter. The detection carrier comprises a coating protein having a recognition site for binding the object of interest, and the reporter comprises a spin luminescent material. A mixture of the reporter and the biological sample is loaded onto the detection carrier. The detection system comprises a time-varied physical field, a light source, a signal acquisition assembly, and a processing device. The detection carrier with the mixture of the reporter molecule and the biological sample is placed in the time-varied physical field. The light source provides an excitation light to irradiate the detection carrier placed in the time-varied physical field so as to excite the spin luminescent material and generate a fluorescence signal modulated by the time-varied physical field. The signal acquisition assembly receives the fluorescence signal. The processing device electrically connects to the time-varied physical field, the light source, and the signal acquisition assembly. The processing device receives the fluorescence signal from the signal acquisition assembly and analyzes the fluorescence signal.

To achieve the above objective, the present disclosure further provides a detection system for detecting an object of interest in a biological sample. The detection system comprises a detection kit, a time-varied physical field, a light source, a signal acquisition assembly, and a processing device. The detection kit comprises a detection carrier and a reporter. The detection carrier comprises a coating protein having a recognition site for binding the object of interest, and the reporter comprises a spin luminescent material. A mixture of the reporter and the biological sample is loaded onto the detection carrier. The detection carrier with the mixture of the reporter molecule and the biological sample is placed in the time-varied physical field. The light source provides an excitation light to irradiate the detection carrier placed in the time-varied physical field so as to excite the spin luminescent material and generate a fluorescence signal modulated by the time-varied physical field. The signal acquisition assembly receives the fluorescence signal. The processing device electrically connects to the time-varied physical field, the light source, and the signal acquisition assembly. The processing device receives the fluorescence signal from the signal acquisition assembly and analyzes the fluorescence signal.

According to an embodiment of the present disclosure, the time-varied physical field comprises an alternating current magnetic field or a microwave field.

According to an embodiment of the present disclosure, a frequency of the alternating current magnetic field is between 1 Hz and 1 MHz, a root mean square value of an amplitude of the alternating current magnetic field is between 1 G and 10000 G, and a frequency of the microwave field is between 0.1 MHz and 10 GHz.

According to an embodiment of the present disclosure, the processing device compares the fluorescence signal with a quantitative standard curve to quantify a concentration of the object of interest.

According to an embodiment of the present disclosure, the signal acquisition assembly comprises a photomultiplier tube, an objective lens, a filter, and a data acquisition component.

As described above, the detection method and detection system of the present disclosure can be used to detect the existence or the characteristics of an object of interest in a biological sample. The detection method comprises the step of providing a detection kit, which comprises a detection carrier and a reporter. The detection carrier has a coating protein having a recognition site for binding the object of interest, and the reporter comprises a spin luminescent material. Thus, in the detection operation, it is necessary only to mix the reporter and the biological sample, load the mixture on the detection carrier, and place the detection carrier into a time-varied physical field provided by the detection system, thereby achieving the effect of simplifying the operation. In addition, the object of interest bound by the reporter can be analyzed through the characteristics of the spin luminescent material that can be irradiated with an excitation light to generate a fluorescence signal. The fluorescence signal generated by the spin luminescent material modulated by the time-varied physical field can avoid background interference, thereby achieving the effect of increasing the sensitivity compared with that of the conventional immunoassay.

DETAILED DESCRIPTION OF THE EMBODIMENTS

In order to make the structure and characteristics as well as the effectiveness of the present disclosure further understood and recognized, a detailed description of the present disclosure is provided as follows, along with embodiments and accompanying figures.

The terms "an embodiment" and "in an embodiment" employed herein mean that the embodiment described may include specific appearance, feature, structure or characteristic, without the limitation that every embodiment must include the specific appearance, feature, structure or characteristic. In addition, the terms can but do not necessarily refer to the same embodiments mentioned in other parts of the specification. Moreover, when a specific module, appearance, feature, structure or characteristic is described and combined into an embodiment, no matter whether or not there is a clear description in the specification, those skilled in the art can still combine the module, appearance, features, structures, or characteristics into other embodiments. In other words, any module, element, or feature can be combined with other elements or features in different embodiments unless it has obviously or inherently incompatible characteristics or is specifically excluded.

First, the detection method and the detection system provided by the present disclosure are a combination of immunoassay and optical methods to detect an object of interest in a biological sample and to do quantitative or qualitative analysis of the object of interest. The object of interest may be an antigen or an antibody. Further, the antigen may be a biological molecule, such as a nucleic acid, protein, or carbohydrate, and may also be a microbe, such as a virus or bacteria. In some embodiments, the biological sample may be a clinical specimen so that the detection method and system can be used for detecting the presence or absence of the object of interest in the specimen and for further quantification of the object of interest. In another embodiment, the biological sample may also be a solution with different (monoclonal) antibodies so that the detection method and system can be used for rapid antibody screening applications and for performing qualitative analysis of the object of interest (i.e., an antibody).

Figure 1:
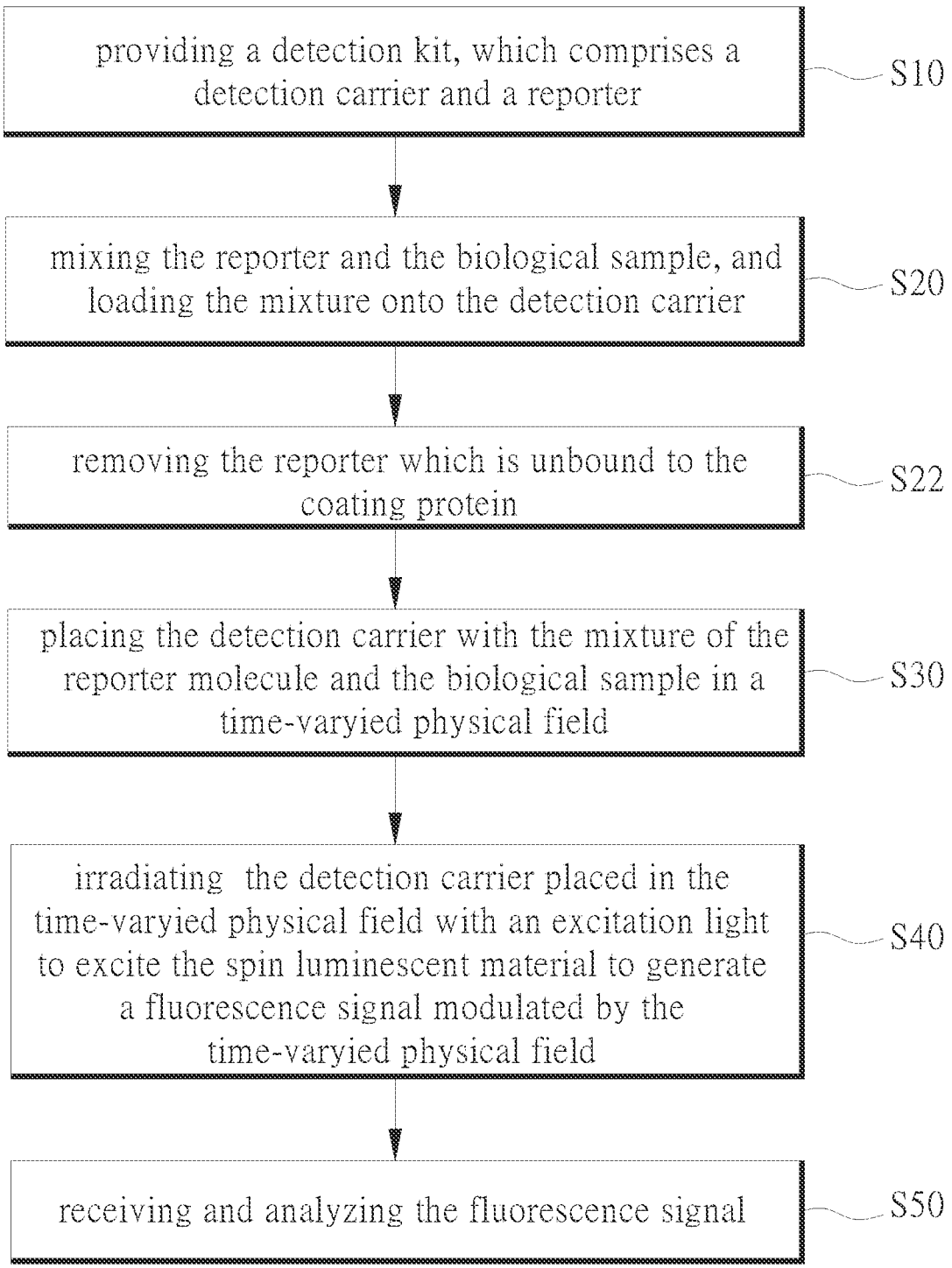
FIG. 1 illustrates a flowchart of a detection method according to an embodiment of the present disclosure.

FIG. 1 illustrates a flowchart of a detection method according to an embodiment of the present disclosure. Please refer to FIG. 1. The detection method of the present embodiment comprises the following steps: providing a detection kit, which comprises a detection carrier and a reporter (in step S10); mixing the reporter and the biological sample, and loading the mixture onto the detection carrier (in step S20); removing the reporter which is unbound to the coating protein (in step S22); placing the detection carrier with the mixture of the reporter molecule and the biological sample in a time-varied physical field (in step S30); irradiating the detection carrier placed in the time-varied physical field with an excitation light to excite the spin luminescent material to generate a fluorescence signal modulated by the time-varied physical field (in step S40); and receiving and analyzing the fluorescence signal (in step S50).

Figure 2A:
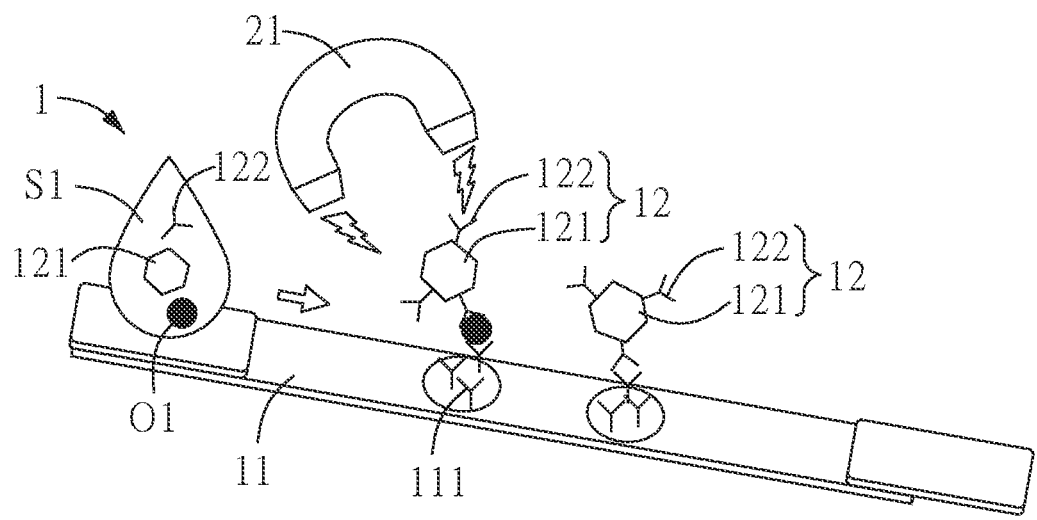
FIG. 2A illustrates a schematic diagram of a detection kit according to the first embodiment of the present disclosure.
Figure 2B:
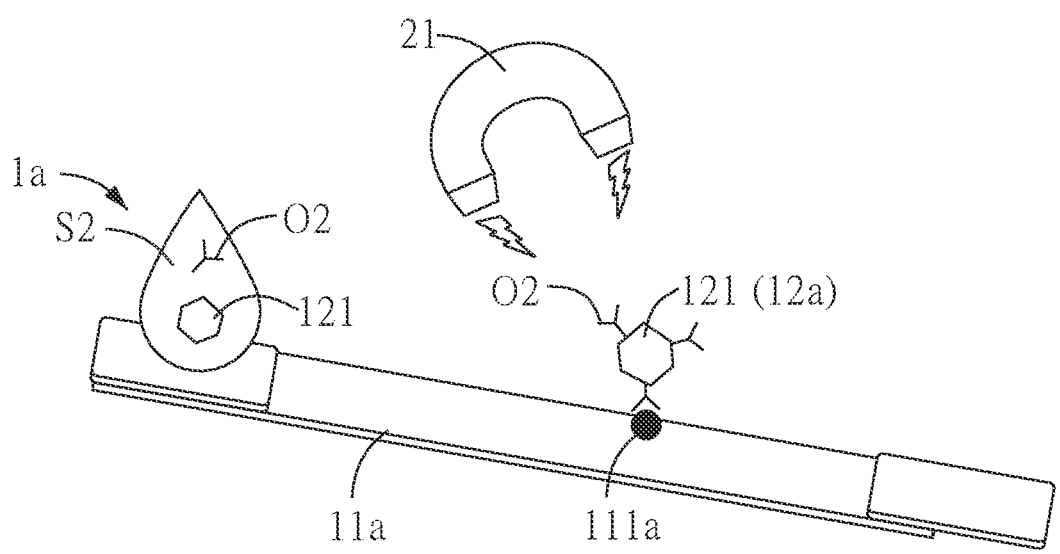
FIG. 2B illustrates a schematic diagram of a detection kit according to the second embodiment of the present disclosure.

FIG. 2A illustrates a schematic diagram of a detection kit 1 according to the first embodiment of the present disclosure, and FIG. 2B illustrates a schematic diagram of a detection kit 1a according to the second embodiment of the present disclosure. Both FIG. 2A and FIG. 2B illustrate step S10 to step S30 as shown in FIG. 1. The following first employs the detection kit 1 of the first embodiment as an example; please refer to FIG. 1 and FIG. 2A. In step S10, a detection kit 1 is provided. The detection kit 1 comprises a detection carrier 11 and a reporter 12, and the detection carrier 11 further comprises a coating protein 111. The coating protein 111 is a kind of protein coated on the detection carrier 11 and is used for detecting and binding an object of interest O1. The coating protein 111 has a recognition site for binding the object of interest O1.

Specifically, the coating protein 111 may be an antibody or an antigen, depending on the experiment to be designed or the kind of the object of interest O1. The coating protein 111a of the detection kit 1 shown in FIG. 2A is an antibody, and the coating protein 111a of the detection kit 1a shown in FIG. 2B is an antigen. In FIG. 2A, for example, the detection kit 1 can be used for detecting a specific foreign substance in the biological sample S1; that is, the object of interest O1 is an antigen. In this case, the coating protein 111 is an antibody. In the first embodiment, the recognition site of the coating protein 111 is a paratope, which can recognize and bind to an epitope of the object of interest O1.

In FIG. 2B, for example, the detection kit 1a of the second embodiment can be used for the qualitative analysis of antibody screening, and the object of interest O2 can be the antibody to be selected, to detect whether the antibody in the specimen can bind to a specific antigen. In this case, the coating protein 111a is the specific antigen. In the second embodiment, the recognition site of the coating protein 111a is an epitope, which can be bound by a paratope of the object of interest O2 (i.e., the monoclonal antibody).

In addition, the detection carriers 11, 11a of the first and second embodiment may comprise a solid phase substrate, such as a membrane or protein coating, and a nitrocellulose membrane (referred to as an NC membrane) is often used. The NC membrane is often used as a strip of the immunoassay. Thus, the detection kits 1, 1a of the first and second embodiments can be applied to a lateral flow immunoassay test (hereinafter referred to as an LFIA test). In another embodiment, the detection carrier may further comprise a liquid phase substrate so that the detection kit can be applied to enzyme-linked immunosorbent assay (hereinafter referred to as ELISA). Specifically, the solid phase substrate of the detection carrier is an ELISA microplate, and the coating protein can be coated on the bottom of the ELISA microplate. The liquid phase substrate is a colorimetric substrate.

The reporter 12 is a substance that is used to label the object of interest O2 and can be excited by light to emit fluorescence. In the first embodiment (shown in FIG. 2A), for example, the reporter 12 comprises a spin luminescent material 121 and a capture antibody 122. The spin luminescent material 121 is a material that can be modulated by a magnetic field and can be excited by light of a specific wavelength to emit fluorescence of a different wavelength. The spin luminescent material 121 may be but is not limited to a fluorescent nanodiamond (hereinafter referred to as an FND), an organic dye-labeled magnetic bead, or a rare-earth metal ion doped magnetic bead. In addition, the spin luminescent material 121 comprises a plurality of spin luminescent particles. Preferably, a diameter of each of the spin luminescent particles is between 1 nm and 1 mm.

The spin luminescent material 121 of this embodiment employs the FND as an example. When the FND (i.e., the spin luminescent material 121) is irradiated with yellow-green light (a wavelength of 500-600 nm), it will emit red light with a wavelength of about 700 nm. Thus, the quantitative or qualitative analysis of the objects of interest O1, O2 can be performed by analyzing the fluorescence intensity of the red light (further described below). In addition, the surface of the FND can easily derive functional groups, such as carboxyl (—COOH) or amine (—NH2), so the FND can be linked to nucleic acids, proteins, or carbohydrates and other biological molecules.

In order to increase the specificity between the reporter 12 and the object of interest O1, the spin luminescent material 121 can conjugate to the capture antibody 122 to form a complex such that the reporter 12 can label the object of interest O1 in the biological sample S1 by the capture antibody 12. Specifically, the capture antibody 122 and the coating protein 111 are the same kind of antibody; both have the recognition site for binding to the object of interest O1. That is, the capture antibody 122 also has the paratope for recognizing and binding to the epitope of the object of interest O1. Thus, the embodiment of the reporter 12 comprising the spin luminescent material 121 and the capture antibody (as shown in FIG. 2A) is suitable for detecting and quantifying the antigen (i.e., the object of interest O1) in the biological sample S1.

In step S20, the reporter 12 and the biological sample S1 are mixed, and the mixture is loaded onto the detection carrier 11. Specifically, after the reporter 12 and the biological sample S1 are mixed, if the object of interest O1 (i.e., antigen) is present in the biological sample S1, the capture antibody 122 of the reporter 12 can capture the object of interest O1 by the specificity of the antibody-antigen. Then the mixture of the reporter 12 and the biological sample S1 is loaded onto the detection carrier 11. At this time, the coating protein 111 (i.e., antibody) on the detection carrier 11 can also capture the object of interest O1 (i.e., antigen) labeled by the reporter 12 by specificity of the antibody-antigen. In other words, the reporter 12 binds to the coating protein 111 via the object of interest O1.

In the second embodiment (as shown in FIG. 2B), for example, the reporter 12a only has the spin luminescent material 121. Because the spin luminescent material 121 is also the FND, it has the same reference numeral as that in the first embodiment. In the second embodiment, a plurality of biological samples S2, which may be solutions with different (monoclonal) antibodies, can be prepared for use in an antibody screening application. In step S20, when the reporter 12a and the biological sample S2 are mixed, the spin luminescent material 121 can bind to the (monoclonal) antibody for detection or selection. In other words, the spin luminescent material 121 binds directly to the object of interest O2.

It should be noted that, in the case of the spin luminescent material 121 being an organic dye-labeled magnetic bead or a rare-earth metal ion doped magnetic bead, the conventional method of preparing the magnetic bead labeled antibody can be used to conjugate the spin luminescent material 121 with the capture antibody 122 or the antibody to be detected (i.e., the object of interest O2).

In step S22, the reporters 12, 12a which are unbound to the coating proteins 111, 111a are removed. The detection kits 1, 1a of the first and second embodiments are applied to the LFIA strip, so the reporters 12, 12a which are unbound to the coating proteins 111, 111a can be removed by the flow characteristics.

In the first embodiment, if the object of interest O1 (i.e., an antigen) is present in the biological sample S1, then when the mixture of the biological sample S1 and the reporter 12 flows through a band deposited with the coating protein 111 (generally called a test line), the object of interest O1 (labeled by the reporter 12) can be bound by the coating protein 111 and stay on the test line. The reporter 12 which is unbound to the coating protein 111 (i.e., the reporter 12 which is unbound to the object of interest O1) flows to a position outside of the test line, such as the end of the strip, to avoid interfering with the quantification of the object of interest O1.

In the second embodiment, if the object of interest O2 (i.e., the antibody to be detected or selected) is bounded by the coating protein 111a (i.e., the specific antigen), the object of interest O2 labeled by the reporter 12a stays on the test line (i.e., the band deposited with the coating protein 111a). The reporter 12a which is unbound to the coating protein 111a indicates that the object of interest O2 is not specific to the coating protein 111a. The reporter 12a which is unbound to the coating protein 111a is removed by the flow characteristics to select the object of interest O2 (i.e., the antibody to be detected or selected), and it is also a qualitative test for the object of interest O2.

In another embodiment, in the case of the detection kit being applied to ELISA, the reporter which is unbound to the coating protein can be removed by the washing steps of the ELISA procedure.

Figure 3:
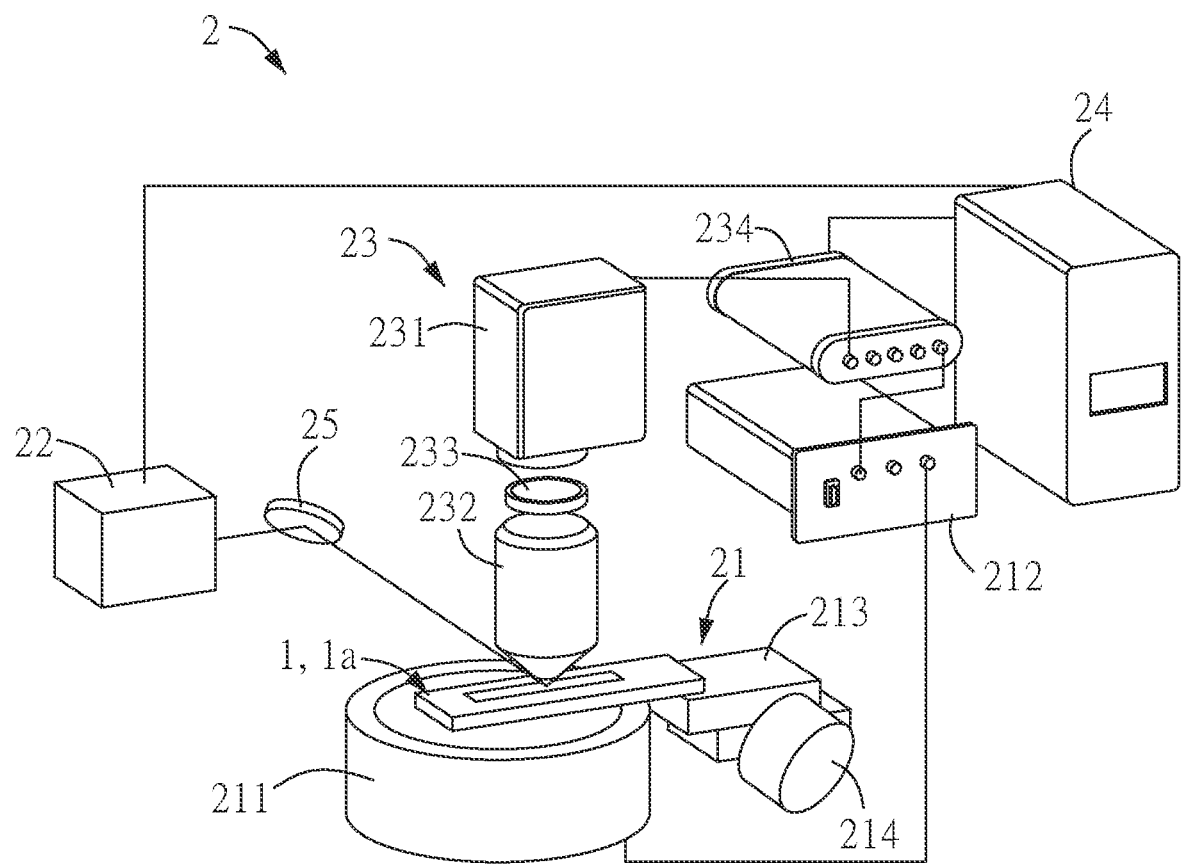
FIG. 3 illustrates a schematic diagram of a detection system according to an embodiment of the present disclosure.

FIG. 3 illustrates a schematic diagram of a detection system according to an embodiment of the present disclosure. Please refer to FIG. 1, FIG. 2A, FIG. 2B and FIG. 3. Both of the detection kits 1, 1a can be placed in the detection system 2 to perform the following steps S30 to S50. In other words, the detection system 2 may be used with the detection kits 1, 1a for detecting the objects of interest O1, O2 in the biological samples S1, S2, and for quantitative or qualitative analysis of the objects of interest O1, O2. In this embodiment, the detection system 2 comprises a time-varied physical field 21, a signal acquisition assembly 23 and a processing device 24. The processing device 24 electrically connects to the time-varied physical field 21, the light source 22 and the signal acquisition assembly 23 to control the components and receives the information of the fluorescence signal.

In the detection kit 1 of the first embodiment, for example, in step S30, the detection carrier 11 with the mixture of the reporter 12 and the biological sample S1 is placed in the time-varied physical field 21. The time-varied physical field 21 may be but is not limited to an alternating current magnetic field (hereinafter referred to as an AC magnetic field) or a microwave field. The time-varied physical field 21 of this embodiment is an AC magnetic field. The time-varied physical field 21 comprises a coil 211 and a current amplifier 212 electrically connected to each other. Further, the current amplifier 212 electrically connects to the processing device 24 via the signal acquisition assembly 23 (details are further described in step S50) such that the processing device 24 can drive the current amplifier 212 to provide an alternating current to the coil 211. The AC magnetic field generated by applying the alternating current to the coil 211 can be regarded as a time-varied electromagnetic field (i.e., the time-varied physical field 21). According to the experimental design, a frequency of the AC magnetic field may be between 1 Hz and 1 MHz, and the root mean square value of an amplitude of the AC magnetic field may be between 1 G and 10000 G. Furthermore, in the case that the time-varied physical field 21 is the microwave field, a frequency of the microwave field is preferably between 0.1 MHz and 10 GHz.

In addition, the time-varied physical field 21 further comprises a translation stage 213, and the translation stage 213 is adjacent to the coil 211. The detection carrier 11 is disposed on the translation stage 213 and can be modulated by the time-varied electromagnetic field generated by the coil 211. Preferably, the translation stage 213 is driven by a stepper motor 214. The stepper motor 214 electrically connects to the processing device 24 such that the processing device 24 can drive the translation stage 213 to move according to a preset path by controlling the stepper motor 214 to scan the detection carrier 11 placed on the translation stage 213.

In step S40, the detection carrier 11 placed in the time-varied physical field 21 is irradiated with an excitation light so as to excite the spin luminescent material 121 to generate a fluorescence signal modulated by the time-varied physical field 21. Specifically, the light source 22 provides the excitation light to irradiate the detection carrier 11 placed in the time-varied physical field 21. The light source 22 may be a laser emitter which can emit laser (i.e., the excitation light) with a wavelength of 500 nm to 600 nm so as to excite the FND (i.e., the spin luminescent material 121) such that it emits a red light with a wavelength of about 700 nm. In another embodiment, laser of a different wavelength may be employed according to the characteristics of the organic dye-labeled magnetic bead or the rare-earth metal ion doped magnetic bead, and the wavelength range is 400 nm to 800 nm.

In addition, the detection system 2 further comprises at least one reflecting mirror 25, which is disposed on the light path between the light source 22 and the translation stage 213, to guide the excitation light to irradiate the detection carrier 11 placed on the translation stage 213. Further, the spin luminescent material 121 is placed in the time-varied physical field 21 together with the detection carrier 11 such that the spin luminescent material 121 can be modulated by the time-varied physical field 21 and emit a fluorescence signal. The fluorescence signal modulated by the time-varied physical magnetic field 21 can be determined to be the fluorescence signal generated by the spin luminescent material 121 after signal analysis in the subsequent step S50, thereby achieving the effect of reducing background interference.

In step S50, the signal acquisition assembly 23 and the processing device 24 receive and analyze the fluorescence signal respectively. In this embodiment, the signal acquisition assembly 23 comprises a photomultiplier tube 231, an objective lens 232, a filter 233 and a data acquisition component 234. The objective lens 232 corresponds to the position of the detection carrier 11 and further corresponds to the test line (i.e., the band on which the coating protein 111 is deposited) of the detection carrier 11 to receive the fluorescence signal generated by the spin luminescent material 121 of the reporter 12. The photomultiplier tube 231 corresponds to the objective lens 232 to enhance the received fluorescence signal. The filter 233 is disposed between the photomultiplier tube 231 and the objective lens 232. In this embodiment, the wavelength of the filter 233 is higher than the wavelength of the excitation light to avoid interference caused by the excitation light.

The data acquisition component 234 electrically connects to the photomultiplier tube 231, the processing device 24 and the current amplifier 212. The data acquisition component 234 receives the fluorescence signals generated by the spin luminescent material 121 from the photomultiplier tube 231 and then performs digital-to-analog conversion of the fluorescence signals. In addition, due to the configuration of the data acquisition component 234 electrically connected to the processing device 24 and the current amplifier 212, the data acquisition component 234 is able to act both as a digital lock-in amplifier and as a function generator. The processing device 24 first generates a digital sequence of voltages that resembles a voltage sinewave of the chosen frequency. The current amplifier 212 electrically is connected to the processing device 24 via the data acquisition component 234 such that the current amplifier 212 is able to output voltage sinewaves with indefinite repetition. In the meantime, the data acquisition component 234 measures the input voltages and sends the digital signals back to the processing device 24. The input and output digital signals undergo mathematical operations to generate lock-in signals.

For example, after analysis of the received signals by Fourier transform or digital lock-in detection, the signal (e.g., the signals of FND) generated by the spin luminescent material 121 can be obtained. Specifically, the electrical signals containing fluorescence information can be fed into either a conventional lock-in amplifier or a data acquisition card (i.e., the signal acquisition assembly 23) for computational phase-sensitive detection. When operating in the latter mode, the detected signal ($V_m$) is first multiplied by 2 reference signals, $\sin(2\pi ft)$ and $\cos(2\pi ft)$, as follows:

$$V_x = V_m \cos(2\pi ft)$$

$$V_y = V_m \sin(2\pi ft).$$

The root mean square (rms) values of Vx and V y are then recorded to produce X and Y, which are used to calculate R, defined as the square root of the sum of $X^2$ and $Y^2$, as follows, which is linearly proportional to the concentration of the reporters 12, 12a.

$$R = \sqrt{X^2 + Y^2}$$

In addition, the phase angle (θ) is also a useful indicator for the lock-in detection and is defined as follows:

$$\theta = \tan^{-1}(Y/X).$$

The above calculation allows the identification and separation of the signals of the spin luminescent material 121 (i.e., FND signals) from background fluorescence signals because, unlike those of other fluorophores, the fluorescence intensities of the signals generated by the spin luminescent material 121 can be magnetically modulated. The phase angles of the individual measurements are collected to construct a phase angle distribution. The observation of a constant angle in the distribution indicates that the signal is not random noise and can be phase-locked, which is the information of the spin luminescent material 121.

In the first embodiment, the processing device 24 receives the fluorescence signals from the signal acquisition assembly 23 and analyzes the fluorescence signals. If a fluorescence signal generated by the spin luminescent material 121 is detected, such detection indicates that the object of interest O1 (i.e., an antigen) is present in the biological sample S1. Thus, the detection kit 1 of the first embodiment can be used for determining the presence or absence of the object of interest O1 in the biological sample S1. Preferably, the detection method of the first embodiment further comprises a step of comparing the fluorescence signal with a quantitative standard curve for quantification of a concentration of the object of interest O1 by the processing device 24. Specifically, a plurality of sample solutions with different concentrations of the reporter 12 (i.e., the spin luminescent material 121) can be prepared by serial dilution, and the fluorescence signal of each concentration of the sample solutions can be measured to obtain a quantitative standard curve. Subsequently, the concentration of the object of interest O1 in the biological sample S1 can be calculated by comparing the quantitative standard curve with the quantitative standard curve.

In the second embodiment, if the fluorescence signal generated by the spin luminescent material 121 is detected, such detection indicates that the object of interest O2 (i.e., an antibody) in the biological sample S2 binds to the coating protein 111a (i.e., an antigen) deposited on the detection carrier 11 due to the specificity of the antibody-antigen. Thus, the detection kit 1a of the second embodiment can be used for antibody screening applications.

Example 1: Preparation of a Detection Carrier and Setup for a Detection System

In this example, the spin luminescent material 121 consists of 100 nm FND particles produced by electron irradiation of synthetic diamond powders (Element Six), followed by thermal annealing, air oxidation, and strong oxidative acid washes.

This example is based on the application of LFIA. A strip used for LFIA is composed of a nitrocellulose membrane (hereinafter referred to as an NC membrane) of 4 mm in width with the test line positioned about 45 mm from the bottom of the strip.

The architecture of the detection system of this example is shown in FIG. 3. The program executed by the processing device 24 can synchronize the data acquisition process and trigger the current amplifier 212 to produce an alternating current (AC) magnetic field with a frequency of 102.4 Hz switching on/off and with a strength (B) of 40 mT (i.e., the root mean square (rms) value of the amplitude is 400 G) to modulate the fluorescence signal generated by FNDs (refer to FIG. 4A and FIG. 4B first).

The light source 22 is a green laser (Coherent, Obis) which excites the FND particles on the solid surface in the presence of the AC magnetic field, and the resulting fluorescence signals are collected by the objective lens 232, filtered by the filter 233 (Semrock filter, 740LP), and detected by the photomultiplier tube 231 (Thorlabs, PMT1001). Further, the objective lens 232 used in this example is a long-working-distance objective lens (Mitutoyo, 20×), which is used to collect the dual frequency fluorescence signals (modulated by a frequency of 204.8 Hz) generated by the FND particles. The electrical signals are finally fed into the processing device 24 through a data acquisition card (National Instrument, USB-4431) and analyzed by a lock-in amplifier. The details of the analysis are as aforementioned and will not be repeated here.

Example 2: Pretreatment of the Biological Sample and the Reporter

Proteins (antigens or antibodies) are noncovalently conjugated with FNDs in phosphate buffered saline (hereinafter referred to as PBS) at pH 7.4. First, solutions containing acid-treated FNDs (1 mg/mL) and the proteins of interest (1 mg/mL) are mixed together at room temperature for 10 min. It should be noted that the proteins of interest may be the capture antibody 122 of the first embodiment or the object of interest O2 (i.e., antibodies to be used for antibody screening) in the biological sample S2 of the second embodiment. Depending on the application, the weight ratio can vary from 10:1 to 100:1. Second, the mixtures are centrifuged at 20,000×g for 5 min to form pellets. After removal of the supernatant, the protein-conjugated FNDs are re-suspended in PBS containing 3% bovine serum albumin (BSA) and stored at 4° C. for subsequent LFIA or ELISA analysis.

The mixture solution of the biological sample S1 (or S2) and the reporter 12 (or 12a) is dropped at the sample pad position and then moves slowly across the test line. Alternatively, the strip can be dipped into the mixture solution in a 96-well plate to achieve the same purpose. All LFIA measurements are performed at room temperature.

Example 3: Detection of the Fluorescence Signals of the FNDs

In example 3, the 100 nm FNDs prepared in example 1 are directly deposited on the NC membrane, placed in the AC magnetic field (strength (B) of 40 mT and modulation frequency of 102.4 Hz) to detect the electronic signals and confirm that the FNDs can be modulated by the time-varied physical field.

Figure 4A:
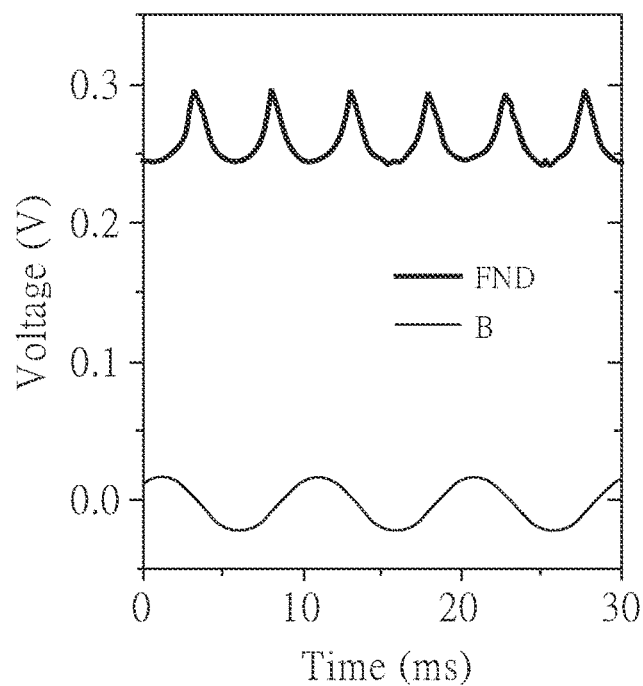
FIG. 4A illustrates electronic signals generated by fluorescent nanodiamonds deposited on a nitrocellulose membrane and modulated by a time-varied physical field.
Figure 4B:
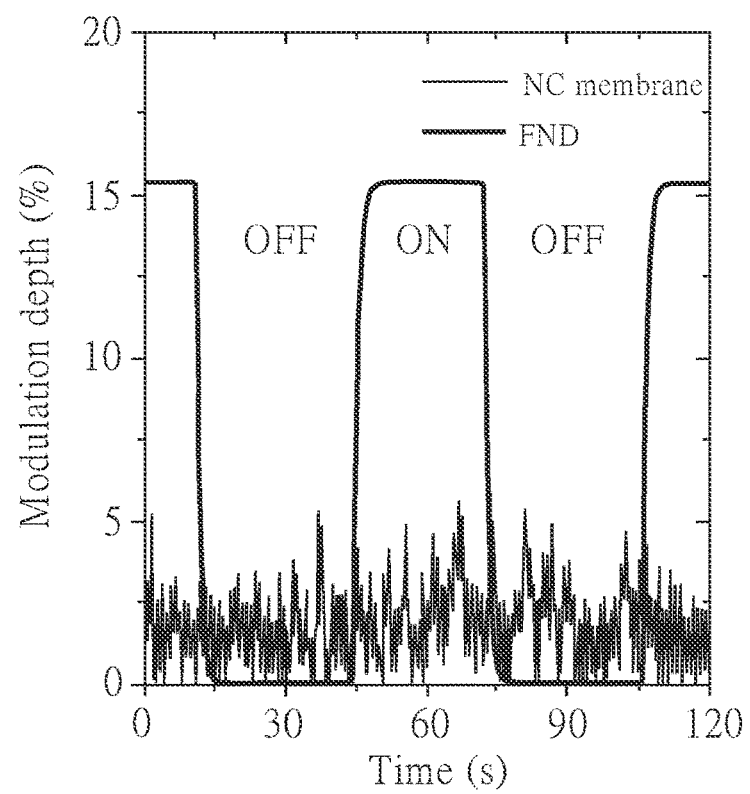
FIG. 4B illustrates the fluorescence intensities of fluorescent nanodiamonds and a nitrocellulose membrane in an alternating current magnetic field On/off.

FIG. 4A illustrates electronic signals generated by FNDs deposited on an NC membrane and modulated by a time-varied physical field; FIG. 4B illustrates the fluorescence intensities of FNDs and an NC membrane in an AC magnetic field on/off. As shown in FIG. 4A, the electronic signals containing fluorescence information generated by the FNDs can change in response to the intensity variations of the AC magnetic field. Thus, the fluorescence signals generated by the FNDs can be modulated by the time-varied physical field. Furthermore, as shown in FIG. 4B, when the AC magnetic field is switched on and off, then although the signal of the NC membrane (control group) will also change, the signal intensity variation of the NC membrane alone is less than the signal intensity variation of the FNDs and even less than 1/1000 of the signal intensity variation of the FNDs. Therefore, the use of the FND as the spin luminescent material 121 of the reporter 12 (or 12a) allows the identification and separation of FND signals from background fluorescence signals (i.e., noise signals).

Figure 4C:
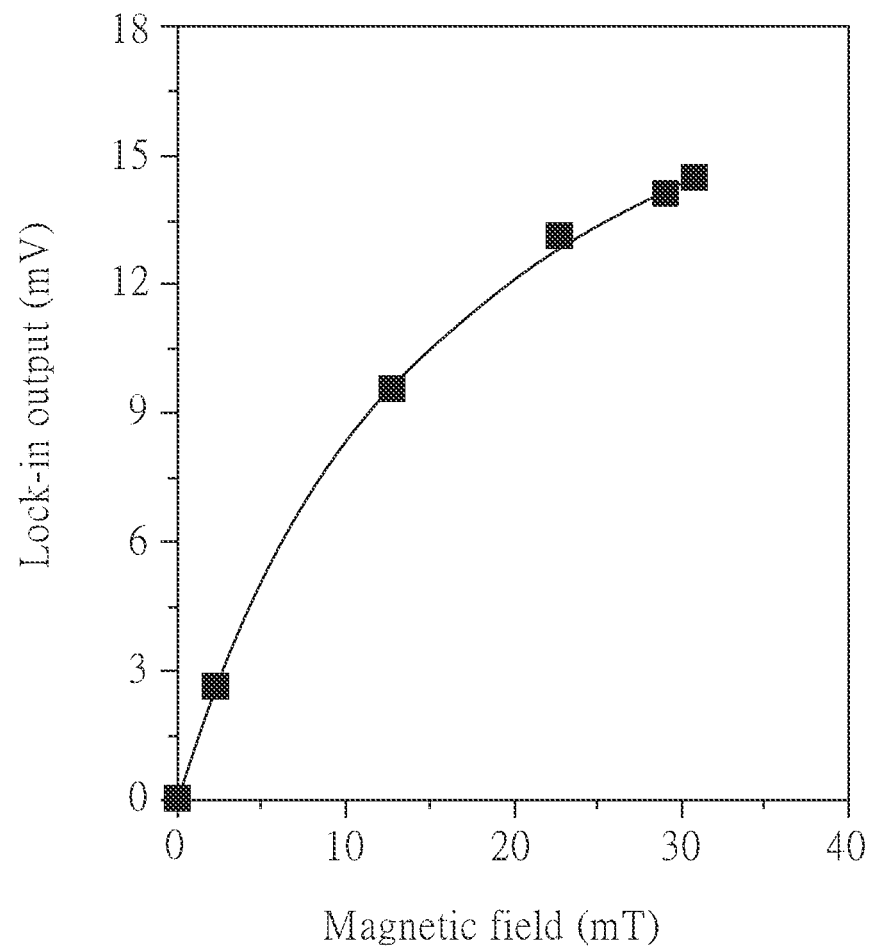
FIG. 4C illustrates the dependence of the modulated fluorescence intensities on the magnetic field strength for fluorescent nanodiamonds on a nitrocellulose membrane.

FIG. 4C illustrates the dependence of the modulated fluorescence intensities on the magnetic field strength for FNDs on an NC membrane. The 100 nm FNDs are also deposited on the NC membrane and placed in the AC magnetic field, and the output electronic signal (i.e., voltage) is analyzed by lock-in detection to find the dependence between the fluorescence intensity and the magnetic field strength. As shown in FIG. 4C, the strength of the (AC) magnetic field (i.e., the root mean square value) of the amplitude is between 1 G and 300 G.

Example 4: Absolute Quantification of FNDs on LFIA Strip

Figure 5A:
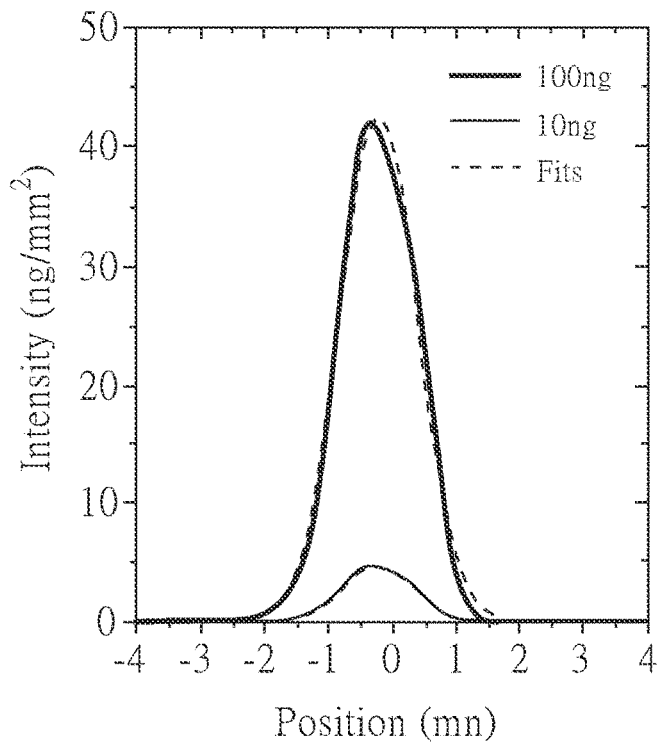
FIG. 5A illustrates a fluorescence signal profile generated by bovine serum albumin-fluorescent nanodiamonds deposited on a nitrocellulose membrane.

According to example 2, the proteins of interest are changed to the bovine serum albumin (hereinafter referred to as BSA) to prepare an aliquot of FNDs conjugated with BSA (hereinafter referred to as BSA-FND). The BSA-FND solutions (0.5 µL each) of 10 ng FNDs and 100 ng FNDs are respectively dropped on LFIA strips and allowed to dry in air. Then the LFIA strips are placed in the AC magnetic field respectively to detect and analyze the fluorescence signals of the BSA-FNDs, and the results as shown in FIG. 5A. FIG. 5A illustrates a fluorescence signal profile generated by BSA-FNDs deposited on a nitrocellulose membrane.

Figure 5B:
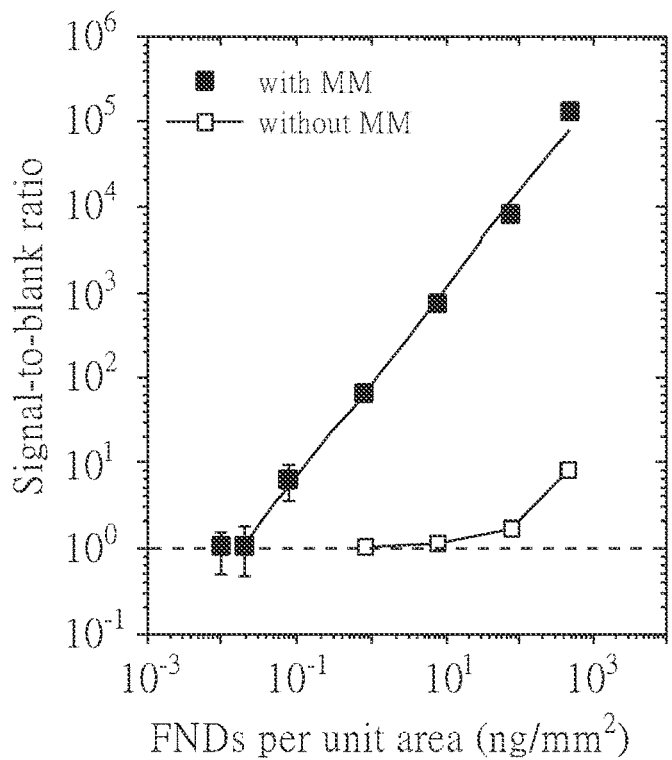
FIG. 5B illustrates a result of an ultrasensitive detection of bovine serum albumin-fluorescent nanodiamonds deposited on a nitrocellulose membrane.

Then BSA-FND solutions of different concentrations and 3% BSA-containing phosphate-buffered saline (as a blank) are respectively dropped in amounts of 0.5 µL on LFIA strips, and the ultrasensitive detection of BSA-FNDs (or BSA) on the strips with and without magnetic modulation (MM) is performed. FIG. 5B illustrates the results of an ultrasensitive detection of BSA-FNDs deposited on the NC membrane. As shown in FIG. 5B, with a condition of a low concentration of FND (e.g., $10^{-2}$ ng/mm$^2$ to $10^3$ ng/mm$^2$), the signal-to-blank ratio of FND modulated by the magnetic field is found to increase linearly with the BSA-FND concentrations over 5 orders of magnitude. The results indicate that the detection method and the detection system of the present disclosure are well suited for quantification.

In addition, the measured limit of detection (LOD) with AC magnetic field modulation (with MM) is 0.01 ng/mm$^2$ or about 5×10$^4$ particles/mm$^2$ for FNDs. Further, the detection sensitivity of fluorescence with AC magnetic field modulation is about 1000-fold higher than the detection sensitivity of fluorescence without magnetic field modulation.

Example 5: Application of FND in Quantitative Analysis

This example employs two model systems, namely, biotin/avidin and human chorionic gonadotropin (hereinafter referred to as hCG), to demonstrate that the detection method and the detection system of the present disclosure can be applied to LFIA strips with (coated) antibodies for antigen detection (that is, the application of the first embodiment) and for antigen quantification.

First, a drop of NeutrAvidin solution (1.5 μL and 5 mg/mL) is added at the center of the NC membrane strip affixed to an absorbent pad to form a band covering the entire cross section of the NC membrane strip. The NeutrAvidin is used as the coating protein 111. Then, according to example 2, the FNDs are coated with biotinylated BSA (hereinafter referred to as B-BSA) at a weight ratio of B-BSA:FND=1:10 in PBS for 10 minutes to form a complex compound of FND-conjugating B-BSA (hereinafter referred to as B-BSA-FND). After centrifugal separation to remove unbound B-BSA, the B-BSA-FNDs are re-suspended in PBS containing 3% bovine serum albumin (BSA).

Figure 6A:
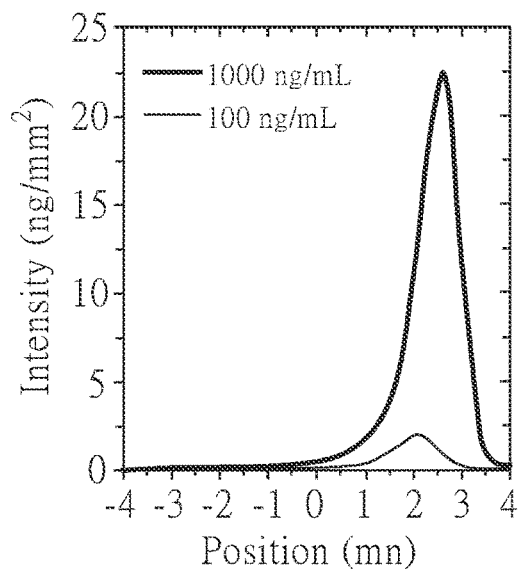
FIG. 6A illustrates a fluorescence signal profile of biotinylated bovine serum albumin-fluorescent nanodiamonds captured by NeutrAvidin on a nitrocellulose membrane.

Further, the NC membrane strip coated with NeutrAvidin is inserted into 100 μL of the B-BSA-FND suspension and dried in air. Then the strip is placed in the detection system of example 1 to detect the electronic signals. FIG. 6A illustrates a fluorescence signal profile of B-BSA-FNDs captured by NeutrAvidin on NC membrane. As shown in FIG. 6A, the NeutrAvidin on the NC membrane can bind to B-BSA-FNDs due to its specificity with biotin, so it can used for detecting and quantifying the biotin by the characteristics of FND.

Figure 6B:
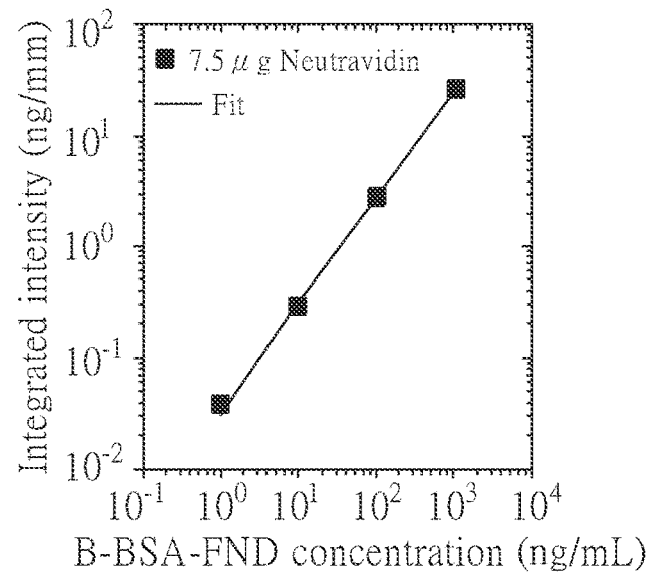
FIG. 6B illustrates integral fluorescence intensities of different concentrations of the biotinylated bovine serum albumin-fluorescent nanodiamonds captured by NeutrAvidin on a nitrocellulose membrane.

Specifically, B-BSA-FND solutions of different concentrations can be prepared to detect the fluorescence intensity, and the fluorescence intensity can be integrated to obtain a curve used for quantification, as shown in FIG. 6B. FIG. 6B illustrates integral fluorescence intensities of different concentrations of the B-BSA-FNDs captured by NeutrAvidin on NC membrane.

In the hCG assay, the commercially available anti-hCG matched pairs, which are purchased from Fitzgerald, are prepared, and the part numbers are 10-C25B (anti-β hCG (B)) and 10-C25D (anti-β hCG(D)). An aliquot (1.5 μL) of anti-β hCG(D) is first deposited on the NC membrane so that the anti-β hCG(D) is used as the coating protein 111.

Figure 6C:
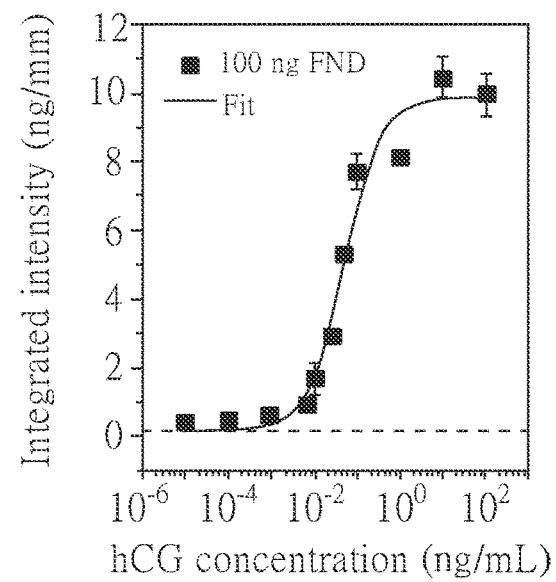
FIG. 6C illustrates an integral fluorescence intensities of different concentrations of anti-β hCG(B)-FND captured by anti-β hCG(D) on a nitrocellulose membrane.

According to the above procedure, sample solutions containing different concentrations of anti-β hCG(B)-FND complex are prepared for detection of the fluorescence intensity, and the fluorescence intensity is integrated to obtain a curve used for quantification, as shown in FIG. 6C. FIG. 6C illustrates integral fluorescence intensities of different concentrations of anti-β hCG(B)-FNDs captured by anti-β hCG(D) on NC membrane. It shows that the detection limit (LOD) of anti-β hCG(B) is about 0.01 ng/mL.

Example 6: Antibody Screening Application of FND

In this example, the hCG model system is used to demonstrate that the detection method and the detection system of the present disclosure can be applied to antibody screening applications (that is, the application of the second embodiment). It should be noted that the second embodiment illustrates the possible situations of practical application, so it describes depositing an antigen (i.e., coating protein 111a) on the detection carrier 11a. The design of example 6 uses anti-hCG matched pairs, so it uses the antibody as the coating protein 111a.

The antibodies used in this example, also purchased from Fitzgerald, have the part numbers of 10-C25B (anti-β hCG (B)), 10-C25D (anti-β hCG(D)), and 10-C25E (anti-β hCG (E)), respectively. First, 1.5 μL of the solution containing anti-β hCG(B), anti-β hCG(D), and anti-β hCG(E) is deposited on different NC membrane strips and at least two copies of each of the antibodies (B, D, E) are prepared. Then the anti-β hCG(B)-FND detection solution containing 10 ng, the anti-β hCG(D)-FND detection solution containing 10 ng, and the anti-β hCG(E)-FND detection solution are prepared according to the above procedure.

Figure 7:
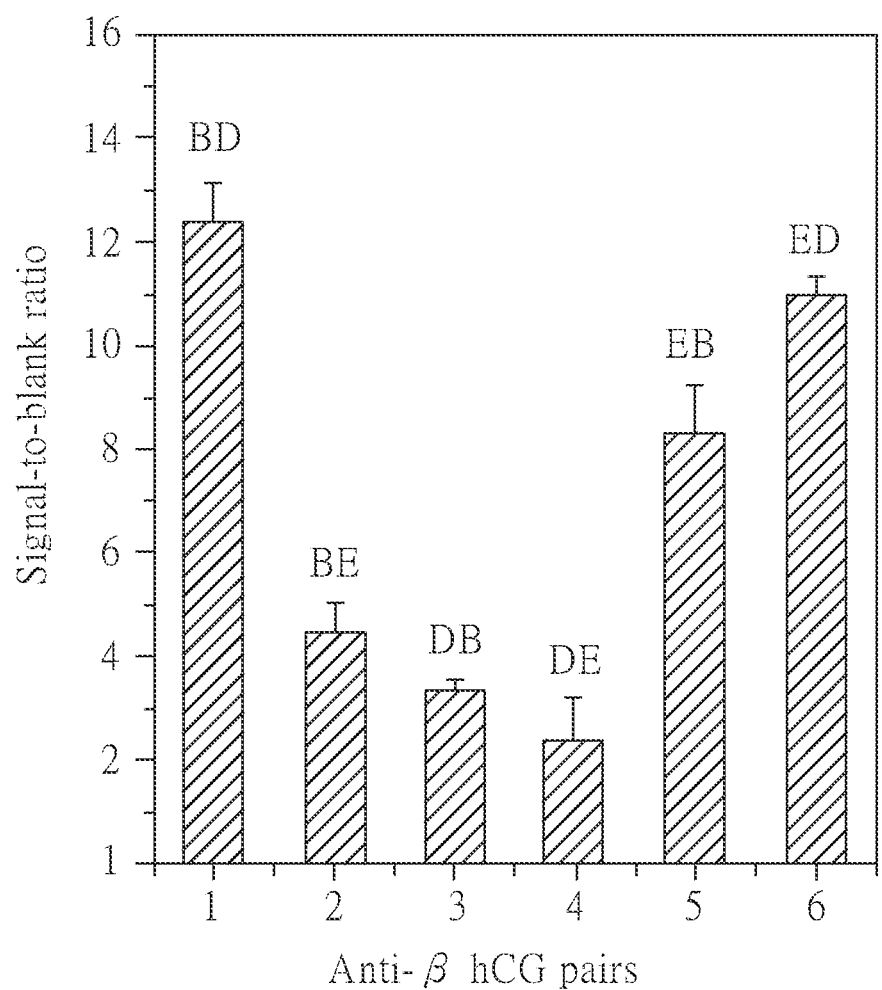
FIG. 7 illustrates the results of fluorescent nanodiamonds being applied to an antibody screening of anti-β hCG matched pairs.

The above NC membrane strips are respectively inserted into detection solutions with different antibodies and after drying are placed in the detection system of example 1 for detection and analysis of the fluorescence signals. The binding ability of the antibody pairs can be analyzed, and the results are shown in FIG. 7. FIG. 7 illustrates the results of the FNDs being applied to an antibody screening of anti-β hCG matched pairs. The first letters in the pairs denote the antibodies deposited on the NC membrane. For example, "BD" in FIG. 7 indicates that the anti-β hCG(B) is deposited on the NC membrane, and the anti-β hCG(D)-FND is contained in the detection solutions.

For example, two NC membrane strips deposited with anti-β hCG(B) are inserted into the detection solution of anti-β hCG(D)-FND and the detection solution of anti-β hCG(E)-FND respectively. After the NC membrane strips dry, they are placed in the detection system for detection of the fluorescence signals of the anti-β hCG(D)-FNDs or anti-β hCG(E)-FNDs captured by the anti-β hCG(B) (i.e, coating protein). As shown in FIG. 7, the pair of anti-β hCG(B) and anti-β hCG(D) has higher affinity and specificity than the pair of anti-β hCG(B) and anti-β hCG(E).

As described above, the detection method and detection system of the present disclosure can be used to detect the existence or the characteristics of an object of interest in a biological sample. The detection method comprises the step of providing a detection kit, which comprises a detection carrier and a reporter. The detection carrier has a coating protein having a recognition site for binding the object of interest, and the reporter comprises a spin luminescent material. Thus, in the detection operation, it is necessary only to mix the reporter and the biological sample, load the mixture onto the detection carrier, and place the detection carrier in a time-varied physical field provided by the detection system, thereby achieving the effect of simplifying the operation. In addition, the object of interest bound by the reporter can be analyzed through the characteristics of the spin luminescent material, which can be irradiated with an excitation light to generate a fluorescence signal. The fluorescence signal generated by the spin luminescent material modulated by the time-varied physical field can avoid background interference, thereby increasing the sensitivity compared with that of the conventional immunoassay.

It should be noted that many of the above-mentioned embodiments are given as examples for description, and the scope of the present invention should be limited to the scope of the following claims and not limited by the above embodiments.

What is claimed is:

1. A detection system, used for detecting an object of interest in a biological sample, the detection system comprising:
    a detection kit, comprising a detection carrier and a reporter, the detection carrier comprising a coating protein having a recognition site for binding the object of interest and the reporter comprising a spin luminescent material, wherein a mixture of the reporter and the biological sample is loaded onto the detection carrier;
    a time-varied physical field, into which the detection carrier with the mixture of the reporter molecule and the biological sample are placed;
    a light source, being configured to provide an excitation light with wavelength ranged from 400 nm to 800 nm, to irradiate the detection carrier placed in the time-varied physical field so as to excite the spin luminescent material and generate a fluorescence signal modulated by the time-varied physical field;

a signal acquisition assembly, comprising a photomultiplier tube and a data acquisition component, the data acquisition component electrically connecting to the photomultiplier tube, the data acquisition component being configured to receive fluorescence signals generated by the spin luminescent material from the photomultiplier tube; and a processing device, electrically connected to the time-varied physical field, the light source, and the data acquisition component of the signal acquisition assembly, the data acquisition component functioning as a lock-in amplifier due to the configuration of the data acquisition component being electrically connected to the processing device, wherein the processing device receives the fluorescence signal from the data acquisition component and analyzes the fluorescence signal.

2. The detection system as claimed in claim 1, wherein the time-varied physical field comprises an alternating current magnetic field or a microwave field.

3. The detection system as claimed in claim 2, wherein a frequency of the alternating current magnetic field is between 1 Hz and 1 MHz, a root mean square value of an amplitude of the alternating current magnetic field is between 1G and 10000 G, and a frequency of the microwave field is between 0.1 MHz and 10 GHz.

4. The detection system as claimed in claim 1, wherein the processing device compares the fluorescence signal with a quantitative standard curve to quantify a concentration of the object of interest.

* * * * *